(12) United States Patent
Vonbehren et al.

(10) Patent No.: US 7,815,924 B2
(45) Date of Patent: Oct. 19, 2010

(54) COSMETIC COMPOSITION CONTAINING MICROCRYSTALLINE CELLULOSE

(75) Inventors: Dale Vonbehren, Shrewsbury, MA (US); Maurice Gerard Lynch, Waterloo (BE); Ana Chordi Miranda, Etterbeek (BE)

(73) Assignee: FMC Corporation, Philadelphia, PA (US)

( * ) Notice: Subject to any disclaimer, the term of this patent is extended or adjusted under 35 U.S.C. 154(b) by 1146 days.

(21) Appl. No.: 10/528,317

(22) PCT Filed: Sep. 18, 2003

(86) PCT No.: PCT/US03/29902

§ 371 (c)(1),
(2), (4) Date: Nov. 14, 2005

(87) PCT Pub. No.: WO2004/026263

PCT Pub. Date: Apr. 1, 2004

(65) Prior Publication Data

US 2006/0115438 A1    Jun. 1, 2006

Related U.S. Application Data

(60) Provisional application No. 60/412,381, filed on Sep. 20, 2002, provisional application No. 60/446,715, filed on Feb. 11, 2003.

(51) Int. Cl.
*A61K 8/02* (2006.01)
*A61K 8/00* (2006.01)
*A61K 9/00* (2006.01)

(52) U.S. Cl. ............................ 424/401; 424/59; 424/400

(58) Field of Classification Search ........................ None
See application file for complete search history.

(56) References Cited

U.S. PATENT DOCUMENTS

| | | | |
|---|---|---|---|
| 3,146,170 A | 8/1964 | Battista | |
| 3,539,365 A | 11/1970 | Durand et al. | |
| 5,188,831 A | 2/1993 | Nicoll et al. | |
| 5,306,485 A | 4/1994 | Robinson et al. | |
| 5,366,742 A | 11/1994 | Tuason et al. | |
| 5,582,815 A | 12/1996 | Appino et al. | |
| 5,607,622 A | 3/1997 | Ueda et al. | |
| 5,858,330 A | 1/1999 | Boltri et al. | |
| 5,935,556 A * | 8/1999 | Tanner et al. | 424/59 |

(Continued)

FOREIGN PATENT DOCUMENTS

CA    2333442 A1    7/2001

(Continued)

OTHER PUBLICATIONS

Notification of Transmittal of the International Search Report or the Declaration—International Filing Date—Sep. 18, 2003—8 Pages.

(Continued)

*Primary Examiner*—Humera N Sheikh (57) ABSTRACT

A sprayable cosmetic composition is disclosed. In one aspect, the composition comprises a sunscreen agent or mixture of sunscreen agents; an emulsifier or mixture of emulsifiers; optionally an emollient or mixture of emollients; a rheology control agent; and water. The rheology control agent is microcrystalline cellulose. When sprayed on the skin or hair, the cosmetic compositions of the invention produce a fine mist that deposits evenly with no dripping and no aggregate or blobs.

15 Claims, 3 Drawing Sheets

U.S. PATENT DOCUMENTS

| | | | |
|---|---|---|---|
| 5,965,112 | A | 10/1999 | Brieva et al. |
| 5,965,179 | A | 10/1999 | Ducret et al. |
| 6,025,007 | A | 2/2000 | Krawczyk et al. |
| 6,037,380 | A | 3/2000 | Venables et al. |
| 6,042,815 | A | 3/2000 | Kellner et al. |
| 6,153,176 | A | 11/2000 | Kaleta et al. |
| 6,165,450 | A | 12/2000 | Chaudhari et al. |
| 6,391,368 | B1 | 5/2002 | Tuason et al. |
| 6,395,269 | B1 | 5/2002 | Fuller et al. |
| 6,497,861 | B1 * | 12/2002 | Wang et al. ............... 424/64 |
| 6,565,832 | B1 | 5/2003 | Haslwanter et al. |
| 6,620,417 | B1 * | 9/2003 | Jose et al. ............... 424/401 |
| 6,841,146 | B2 | 1/2005 | Haslwanter et al. |
| 7,094,448 | B2 | 8/2006 | Ono et al. |
| 7,264,795 | B2 * | 9/2007 | Pflucker et al. ............ 424/59 |
| 2002/0065328 | A1 | 5/2002 | Dederen et al. |
| 2003/0007944 | A1 | 1/2003 | O'Halloran et al. |
| 2004/0115142 | A1 | 6/2004 | Sherwood et al. |
| 2004/0156811 | A1 | 8/2004 | Lynch |
| 2005/0244346 | A1 | 11/2005 | Nakao et al. |

FOREIGN PATENT DOCUMENTS

| | | |
|---|---|---|
| DE | 10008836 A1 | 2/2000 |
| EP | 0780127 A1 | 5/1996 |
| EP | 0780127 A1 | 6/1997 |
| EP | 1036799 A1 | 3/1998 |
| EP | 1532971 A1 | 5/2005 |
| FR | 2711918 A1 | 5/1995 |
| GB | 1 006 706 | 10/1965 |
| GB | 1006706 | 10/1965 |
| JP | 9-241115 | 3/1996 |
| JP | 2003-73229 | 9/2001 |
| WO | WO-9746243 A1 | 12/1997 |
| WO | WO-01/45671 A2 | 6/2001 |
| WO | WO-01/95882 A1 | 12/2001 |
| WO | WO-2004105704 A2 | 12/2004 |

OTHER PUBLICATIONS

Notification of Transmittal of International Preliminary Examination Report—Date of Mailing—Oct. 21, 2004—International Filing Date—Sep. 18, 2003—6 Pages.

FMC Poster Reprint—John Signorin, et al., Safety Evaluation of Co-Processed MCC-CMC (AVICEL® RC-591) as an Excipient in Intra-Nasal Dosage Forms, Present at the 25$^{th}$ International Symposium on Controlled Release of Bioactive Materials Las Vegas, USA, Jun. 21-26, 1998.

Polireddy Dondeti—In Vivo Evaluation of Spray Formulations of Human Insulin for Nasal Delivery, International Journal of Pharmaceutics, vol. 122, pp. 91-105, 1995.

Sunscreens: Development, Evaluation, and Regulatory Aspects, Second Edition, Chapter 18; pp. 353-397; 1997.

Supplementary European Search Report, Dated Aug. 26, 2008, Application No. 03759413.2-2108 / 1539098 PCT/US0329902.

Japanese Examination Report Re JPA 2004-538428 dated Feb. 19, 2008.

* cited by examiner

COSMETIC COMPOSITION CONTAINING MICROCRYSTALLINE CELLULOSE

CROSS-REFERENCE TO RELATED APPLICATIONS

This application claims priority on U.S. Provisional Application 60/412,381, filed Sep. 20, 2002, and U.S. Provisional Application 60/446,715, filed Feb. 11, 2003, both of which are incorporated herein by reference.

FIELD OF THE INVENTION

This invention relates to cosmetic compositions. In particular, this invention relates to sprayable cosmetic compositions that comprise microcrystalline cellulose rheology control agents.

BACKGROUND OF THE INVENTION

Cosmetic compositions, such as sunscreens, self-tanning compositions, after-sun moisturizing compositions, and depilatories, produce a cosmetic, protective, moisturizing, softening, and/or soothing effect when applied to the human skin. Sunscreen compositions, for example, are applied to the skin to protect the skin from the sun's ultraviolet rays that produce erythema, a reddening of the skin commonly known as sunburn. Ultraviolet radiation in the wavelength range of 290 nm to 320 nm ("UV-B"), which is absorbed near the surface of the skin, is the primary cause of sunburn. Ultraviolet radiation in the wavelength of 320 nm to 400 nm ("UV-A") penetrates more deeply into the skin and can cause damaging effects that are more long term in nature. Prolonged and constant exposure to the sun may lead to actinic keratoses and carcinomas as well as to premature aging of the skin, characterized by skin that is wrinkled, cracked, and has lost its elasticity.

Sunscreen agents, which can be divided into two classes, organic and inorganic, can be formulated into various formats of cosmetic products including creams, lotions, sticks, gels and sprays. A highly desirable method for delivering a cosmetic composition, such as a sunscreen composition, to the skin and hair is in the form of a finely dispersed spray. A finely dispersed spray produces improved coverage of the skin and hair and allows easier application to difficult to reach areas. Such a spray is desirably delivered using a non-aerosol spray pump, which does not require the use of pressurized containers or special aerosolizing gases.

The ability of pump-driven delivery systems to deliver a cosmetic composition as a finely divided spray is critically dependent upon the rheology of the cosmetic composition, particularly its viscosity at the exit port of the spray pump. As the viscosity of the composition decreases at the exit port, the spray pattern becomes more divided and produces a more desirable delivery by evenly covering a large area. Conversely, as the viscosity increases, the spray pattern becomes less divided and more stream-like, yielding a less desirable delivery, either by covering only a small area or by unevenly covering a larger one.

The effectiveness of sunscreen compositions and other cosmetic compositions is influenced by their rheology under both high and low shear conditions (see, for example, *Sunscreens. Development, Evaluation and Regulatory Aspects*, N. J. Lowe, N. A. Shaath and M. A. Pathak, Eds, Marcel Dekker, 1997). Sunscreen compositions having low viscosity at high shear rates tend to be easy to spread on the skin and can produce more even coverage and, hence, higher sun protection factors. However, these compositions have a number of deficiencies. They tend to drip or run after application and thus need to be spread immediately after application. This undesirable tendency to run after application can result in the composition dripping into the eyes, especially the eyes of children, or dripping onto clothing. Furthermore, if the viscosity remains low after spreading, the compositions tend to run off the ridges of the skin and accumulate in wrinkles resulting in uneven protection and low sun protection factors.

To overcome these deficiencies, sunscreen compositions are often formulated to have high viscosities. However, high viscosity compositions are more difficult to spread evenly on the skin, resulting in reduced protection from ultraviolet radiation, and often have a heavy skin-feel in addition to the delivery problems encountered with the spray pattern.

Although both oil-in-water and water-in-oil emulsions are used as delivery vehicles, sprayable sunscreen compositions are typically oil-in-water emulsions because of advantages in terms of skin-feel, cost-in-use, and formulation convenience. Stable oil-in-water emulsions are difficult to prepare at very low viscosities. In addition, at very low viscosity it is difficult to achieve good long term suspension of inorganic sunscreen agents, such as titanium dioxide or zinc oxide, that reflect, scatter, and/or absorb ultraviolet radiation and prevents it from reaching the skin and hair. For the inorganic sunscreen to effectively block the ultraviolet radiation, it must be dispersed in the sunscreen composition, in either the oil phase or the aqueous phase.

To improve the water resistance of the sunscreen composition, an emulsion that is stable in the container but breaks down rapidly on shearing is formulated. When an oil-in-water emulsion is delivered to the skin, the water evaporates leaving an oil layer. If the original emulsion is stable to shear, the oil layer will be re-emulsified on wetting of the skin and will be washed off. However, if the original emulsion was unstable to shear, it will break down on spreading and will not be re-emulsified when the skin becomes wet and, thus, will remain on the skin. Typically, emulsions unstable to shear require formulation of an emulsion with a minimum level of emulsifier. This can produce storage stability problems.

High levels of sunscreen agents are required to produce sunscreen compositions with high sun protection factors. This creates formulation difficulties as the organic sunscreen agents must be solubilized and emulsified and the inorganic sunscreen agents must be dispersed and suspended in the sunscreen composition. In addition, all sunscreen agents are expensive.

Thus, a need exists for a sunscreen composition that remains a stable emulsion or suspension during storage in the container and yet has a sufficiently low viscosity when sheared so that it can be effectively delivered as a fine spray using a non-aerosol spray pump and will then resist the tendency to drip.

SUMMARY OF THE INVENTION

The invention is a composition useful as a cosmetic composition. The composition comprises:
  a cosmetic agent or mixture of cosmetic agents;
  an emulsifier or mixture of emulsifiers;
  a rheology control agent; and
  water;
  in which:
  the cosmetic agent or mixture of cosmetic agents comprises about 0.1 wt % to 40 wt % of the composition;
  the emulsifier or mixture of emulsifiers comprises about 0.2 wt % to about 20 wt % of the composition;

the rheology control agent comprises about 0.2 wt % to about 5 wt % of the composition;

the rheology control agent is microcrystalline cellulose having an average particle size of 50 microns or less;

the composition has a viscosity at high shear of 120 Pa s or less, and the composition has a rundown time of 100 seconds or greater.

Other ingredients that are conventional components of cosmetic compositions may also be present in the composition. When sprayed, the compositions of the invention produce a fine mist that deposits evenly with no dripping and no aggregate (blobs). When the compositions are sprayed on a vertical surface, the compositions do not sag or flow.

DETAILED DESCRIPTION OF THE INVENTION

Unless the context indicates otherwise, in the specification and claims, the terms, cosmetic agent, sunscreen agent, emulsifier, emollient, colorant, preservative, skin conditioner, and similar terms also include mixtures of such materials. Unless otherwise specified, all percentages are percentages by weight. The formulation of sunscreen compositions is disclosed in *Harry's Cosmeticology*, 8th Ed., M. M. Rieger, Ed, Chemical Publishing Co., New York, N.Y., 2000; Chaudhuri, U.S. Pat. No. 6,165,450; and Fuller, U.S. Pat. No. 6,395,269, all of which are incorporated herein by reference.

The cosmetic composition comprises microcrystalline cellulose as a rheology control agent. Microcrystalline cellulose is a purified, partially depolymerized cellulose that is generally produced by treating a source of cellulose, preferably alpha cellulose in the form of a pulp from fibrous plants, with a mineral acid, preferably hydrochloric acid. The acid selectively attacks the less ordered regions of the cellulose polymer chain, thereby exposing and freeing the crystallite sites, forming the crystallite aggregates which constitute microcrystalline cellulose. These are then separated from the reaction mixture and washed to remove degraded by-products. The resulting wet mass, generally containing 40 to 60 wt % water, is referred to as hydrolyzed cellulose, microcrystalline cellulose, microcrystalline cellulose wetcake, or simply wetcake.

As described in Ha, U.S. Pat. No. 5,769,934, microcrystalline cellulose may also be produced by steam explosion treatment. Wood chips or other cellulosic materials are placed in a chamber into which super-heated steam is introduced. After about 1-5 minutes, the exit valve is opened rapidly, releasing the contents explosively and yielding microcrystalline cellulose. No additional acid need be introduced into the reaction mixture.

Colloidal microcrystalline cellulose is obtained by reducing the particle size of microcrystalline cellulose and stabilizing the attrited particles to avoid formation of hard aggregates. The method of drying, i.e., removing the water from the wet cake, may be any method which ultimately produces a reconstitutable powder. Techniques for reducing the particle size of microcrystalline cellulose and/or for spray drying microcrystalline cellulose are disclosed in Durand, U.S. Pat. No. 3,539,365; Krawczyk, U.S. Pat. No. 6,025,037; Venables, U.S. Pat. No. 6,037,080, and Tuason, U.S. Pat. No. 6,392,368.

Spray drying of attrited microcrystalline cellulose with one or more co-processing agents can be used to produce microcrystalline cellulose co-processed with a binder. Co-processing agents include, for example, binders such as carboxymethylcellulose, sodium salts of carboxymethylcellulose, calcium salts of carboxymethylcellulose, xanthan gum, carrageenans, alginates, hydroxypropylmethyl cellulose, hydroxypropyl cellulose, hydroxyethyl cellulose, and acrylic acid starch; surfactants such as sodium lauryl sulfate; attriting agents or particulates such as calcium carbonate, zinc oxide, and titanium oxide; and bulking agents such as starches and sugars such as maltodextrin. Co-processing with a binder such as carboxymethylcellulose can be used to produce water-dispersible microcrystalline cellulose.

The preferred microcrystalline cellulose has an average particle size below about 100 microns. More preferably, the microcrystalline cellulose has been attrited to or has an average particle size of below 10 microns, most preferably below 1 micron. The particle size of microcrystalline cellulose can be determined using a Horiba Cappa 700 particle size analyzer. However, as long as sufficient colloidal microcrystalline cellulose is present in the cosmetic composition to control rheology, the composition may also comprise larger microcrystalline particles, for example, particles that have not been attrited or only partially attrited, provided the composition does not become grainy.

Colloidal celluloses comprising microcrystalline cellulose and sodium salt of carboxymethylcellulose are commercially available. AVICEL® RC-581 and AVICEL® RC-591 each contain microcrystalline cellulose and sodium carboxymethylcellulose in a ratio of 89/11, by weight. AVICEL® CL-611 contains microcrystalline cellulose and sodium carboxymethylcellulose in ratio of 85/15, by weight. A preferred rheology control agent is AVICEL® CL-611, which has an average particle size, as determined with a Horiba Cappa 700 particle size analyzer, of less than 1 micron. AVICEL® PC 611, which is also a preferred microcrystalline cellulose, is similar to AVICEL® CL 611. These water dispersible microcrystalline celluloses are available from FMC, Philadelphia, Pa., USA.

The rheology control agent typically comprises about 0.2 wt % to about 5 wt %, preferably about 1 wt % to about 3 wt %, of the cosmetic composition.

The resulting cosmetic composition is sprayable but has a high run-down time so it does not readily run when applied to the skin. Spraying typically does not produce an aerosol. The composition has a viscosity at high shear (2000 s$^{-1}$) of 120 Pa s or less, typically a viscosity at high shear of 100 Pa s or less, more typically a viscosity at high shear of 80 Pa s or less. The run-down time on a vertical surface is typically 100 seconds or greater, more typically 300 sec or greater. Run-down time is determined as described in the Examples below. The composition has an even spray characteristic, that is, when sprayed, the spray extends evenly over a wide area and does not deposit in a collection of small individual drops.

Figure 1:
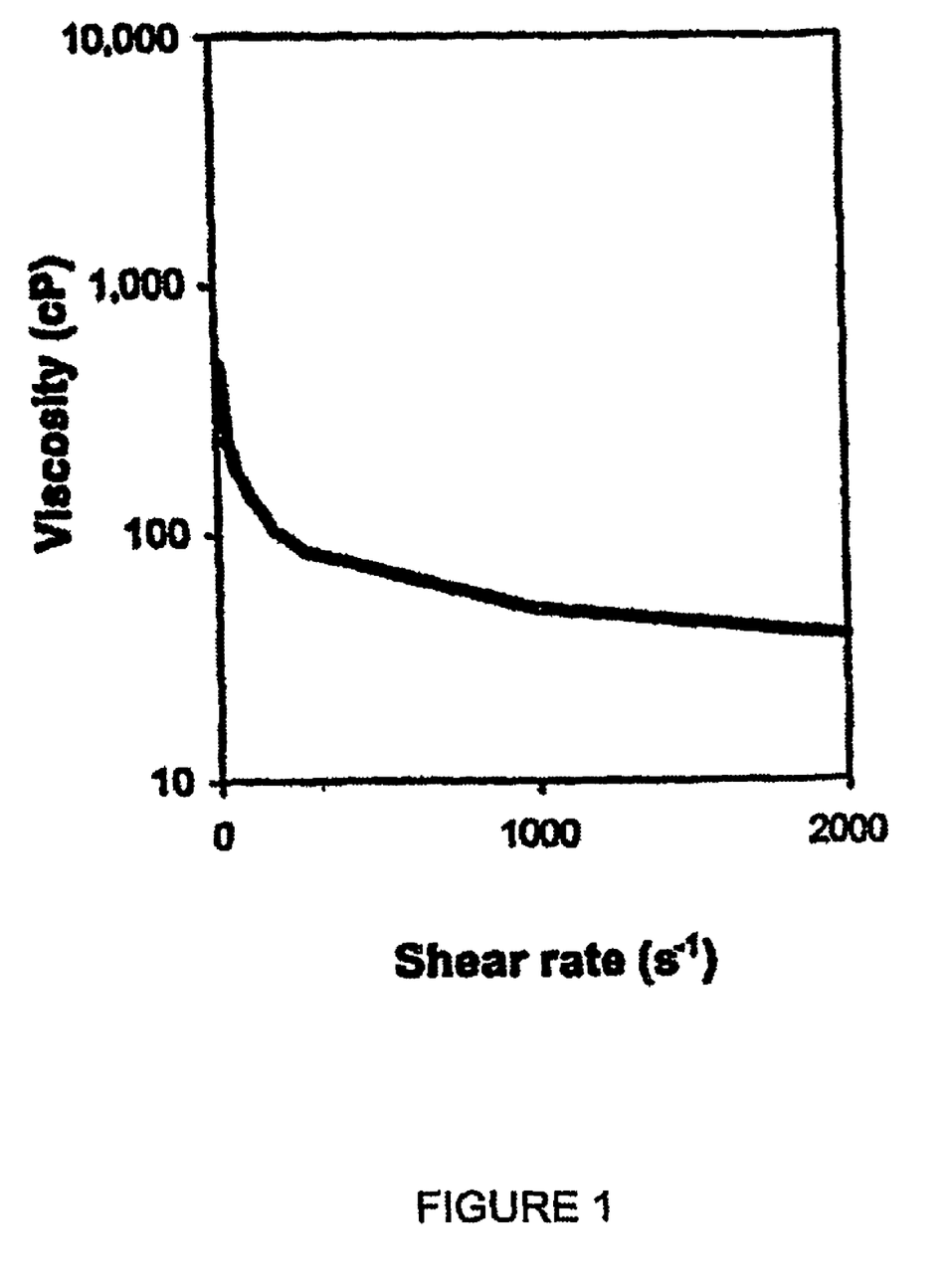
FIG. 1 shows viscosity as a function of shear rate for a cosmetic composition comprising microcrystalline cellulose.
Figure 2:
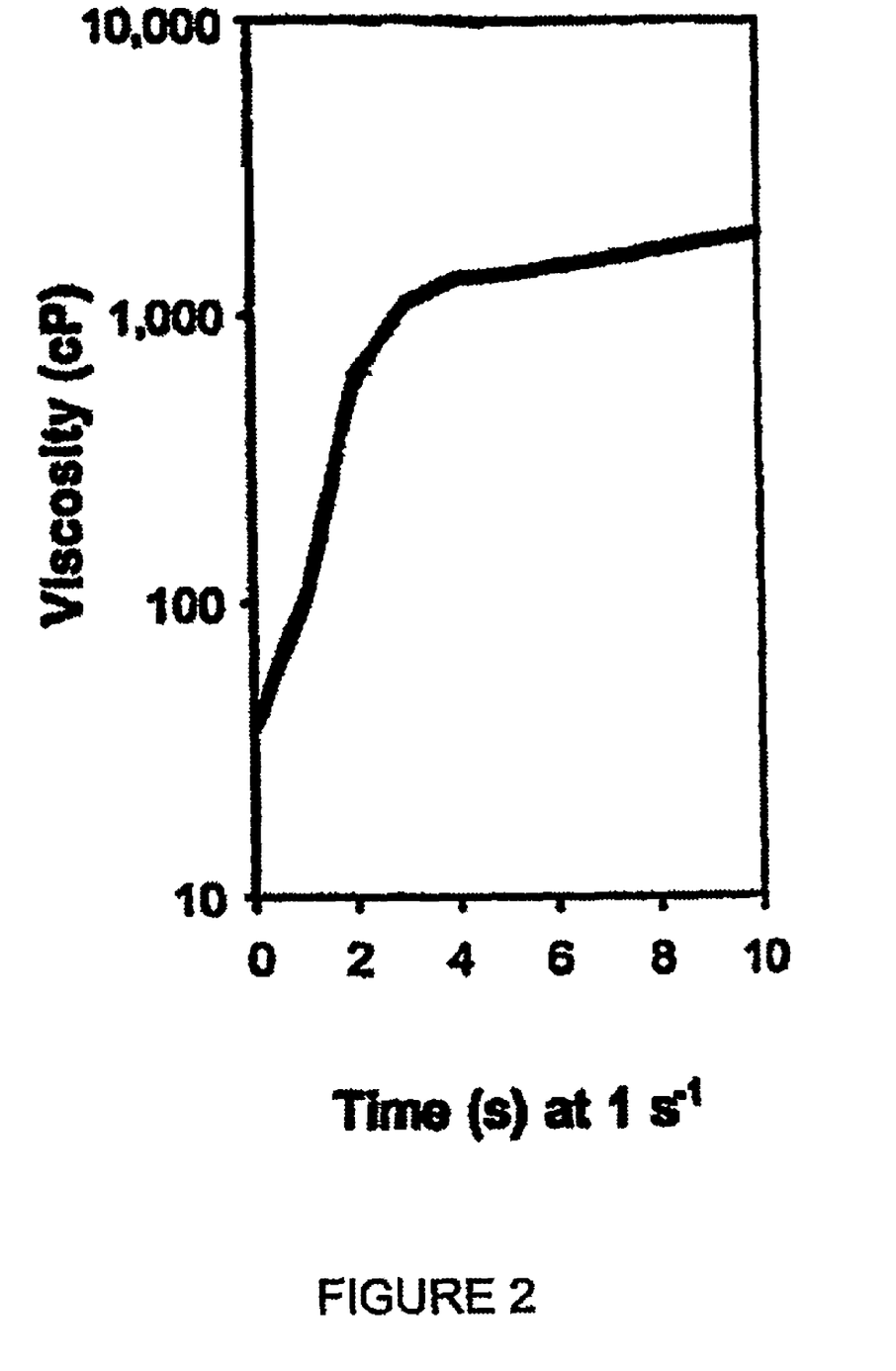
FIG. 2 shows the recovered viscosity as a function of time for a microcrystalline cellulose containing composition.
Figure 3:
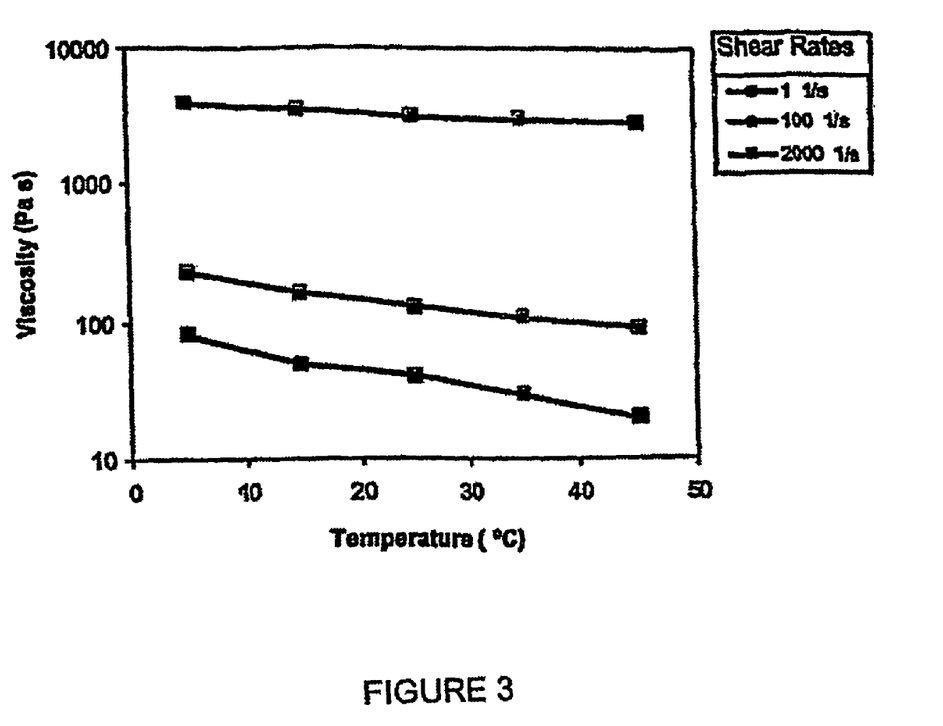
FIG. 3 shows the viscosity as a function of temperature for a microcrystalline cellulose containing composition subjected to different shears.

FIG. 1 shows that the viscosity of a cosmetic composition containing microcrystalline cellulose decreases as the shear increases, such as, for example, when the composition passes through the nozzle of a sprayer. FIG. 2 shows the recovered viscosity, the viscosity after the viscosity has been has been reduced by the application of a high shear of about 2000 s$^{-1}$ and the high shear removed by, for example, passing through the nozzle of a sprayer, as a function of time for a microcrystalline cellulose containing composition. The viscosity rapidly increases in the absence of the high shear when, for example, the composition has been sprayed onto the skin. This rapid increase in viscosity prevents dripping of the composition. FIG. 3 shows the effect of temperature on a composition that contains microcrystalline cellulose either in the container ($1\ s^{-1}$), during spreading on the skin ($10\ s^{-1}$), and during spraying ($2000\ s^{-1}$). The cosmetic composition used for these measurements is described in Example 14.

While not being bound by any theory or explanation, it is thought that microcrystalline cellulose forms a three dimensional network of sub-micron sized insoluble rod-like particles. This network imparts physical stability to an emulsion at low shear rates (e.g., in the container), but rapidly shear thins to from a low viscosity mist on spaying (i.e., when subjected high shear). Because the three dimensional structure rebuilds rapidly when the mist reaches the skin (i.e., at low shear), the sunscreen has desirable non-drip characteristics while having a light skin-feel and easy spreadability.

The cosmetic composition comprises a cosmetic agent or mixture of cosmetic agents. Cosmetic agents produce a cosmetic, protective, moisturizing, softening, and/or soothing effect when applied to human skin. Cosmetic agents include for example, emollients; occlusive agents; moisturizers; humectants; sunscreen agents; skin conditioners, such as panthenol; self-tanning agents such as dihydroxyacetone; agents that remove hair (depilatories), such as mercaptans, especially salts of thioglycolic acid, such as calcium thioglycolate; and exfoliating agents, for example alpha- and beta-hydroxy acids such as lactic acid and glycolic acid, benzoyl peroxide, resorcinol, proteolytic enzymes, retinol and other similar compounds capable of causing desquamation of outer skin layers.

The composition may comprise a cosmetic agent or a mixture of cosmetic agents for moisturizing the skin and reducing moisture loss from the skin. Occlusive agents, such as mineral oil, physically prevent or reduce moisture loss from the skin by formation of a water-impenetrable barrier over the stratum comeum. Humectants and moisturizers attract and hold water to the outside surface and upper layers of the stratum comeum. (Stratum comeum refers to the outer exposed layer of the epidermis). Emollients provide a softening or soothing effect on the skin surface and help control the rate of water evaporation and the tackiness of the composition.

Suitable humectants are, for example, glycerin, polyethylene glycol, polypropylene glycol, sorbitol, and PEG-4. Typical emollients are, for example, lanolin oil; coconut oil; cocoa butter; olive oil; jojoba oils; castor oil; esters such as diisopropyl adipate, hydroxybenzoate esters such as $C_9$-$C_{15}$ benzoate, $C_{12-15}$ alkyl benzoate, iso-nonyl iso-nanoate, diocyl adipate, octyl stearate, hexyl laurate, coco-caprylate caprate, cetaryl isononanoate, isopropyl myristate, propylene glycol dicaprylate/dicaprate, octyldodecyl neopentanoate and propylene glycol isoceteth-3 acetate, decyl oleate, and caprylic/capric triglycerides; cyclomethicone; dimethcone; phenyltrimethicone; alkanes such as mineral oil, silicones such as dimethyl polysiloxane, and ethers such as dicapryl ether; polyoxypropylene butyl ethers, and polyoxypropylene cetyl ethers. A preferred emollient is $C_{12-15}$ alkyl benzoate. When these agents or a mixture of these agents is present as the cosmetic agent, or as part of a mixture of cosmetic agents, these agents typically comprises about 2 wt % to about 25 wt %, preferably about 2 wt % to about 20 wt %, and most preferably about 4 wt % to about 15 wt %, of the composition.

When the composition is a sunscreen composition, it comprises a sunscreen agent. Sunscreen agents absorb, reflect, and/or scatter ultraviolet radiation in the range of 290 nm to 400 nm and thus prevent the ultraviolet radiation from reaching the skin and hair. In addition, the sunscreen agent must be non-toxic and non-irritating when applied to the skin and hair as well as compatible with other ingredients in the sunscreen composition.

Sunscreen agents can be divided into two categories: (1) materials that absorb ultraviolet radiation, typically organic compounds, and (2) materials that reflect, scatter, and absorb ultraviolet radiation, typically inorganic materials. Mixtures of sunscreen agents, including mixtures of both types of sunscreen agents, may be used.

Materials that reflect, scatter, and/or absorb ultraviolet radiation, sometimes referred to as physical sunscreen agents or inorganic sunscreen agents, are typically inorganic materials, such as microfine surface treated titanium dioxide and microfine untreated and surface treated zinc oxide. Titanium dioxide may have an anatase, rutile, or amorphous structure and preferably has a mean primary particle size of between 5 nm and 150 nm, preferably between 10 nm and 100 nm, and more preferably between 15 nm and 75 nm. Zinc oxide preferably has a mean primary particle size of between 5 nm and 150 nm, preferably between 10 nm and 100 nm, and more preferably between 15 and 75 nm.

The titanium dioxide is typically surface treated to prevent photocatalytic reactions that bleach the skin. The coating may be a hydrophilic, hydrophobic, or amphoteric coating. Zinc oxide may be coated to increase ease of dispersion in the sunscreen composition. These agents are sometimes sold as predispersions to avoid the need for high shear homogenization during preparation of the sunscreen composition. Suitable hydrophobically modified titanium dioxide compositions include, for example, UV-TITAN® X161, M160, and M262 (titanium dioxide treated with stearic acid and alumina) (Kemira Pigments, Pori, Finland); T-COTE® (titanium dioxide treated with dimethicone) (SunSmart, Wainscott, N.Y., USA), and MIRASUM® TiW60 (titanium dioxide treated with silica and alumina) (Rhone-Poulenc, Cranbury N.J., USA). Suitable zinc oxides include, for example, Z-COTE® (uncoated microfine zinc oxide) (SunSmart); and Z-COTE® HP-1 (zinc oxide treated with dimethicone) (SunSmart).

Organic materials that absorb ultraviolet radiation, referred to as organic sunscreen agents, include, for example, p-aminobenzoic acid (PABA); benzophenone-1 (2,4-dihydroxybenzophenone); benzophenone-2 (2,2',4,4'-tetrahydroxybenzophenone); benzophenone-3 (2-hydroxy-4-methoxybenzophenone); benzophenone-4 (2-hydroxy-4-methoxybenzophenone-5-sulfoninc acid); benzophenone-6 (2,2'-dihydroxy-4,4'-dimethoxybenzophenone); benzophenone-8 (2,2'-dihydroxy-4-methoxybenzophenone), benzophenone-12 (2-hydroxy-4-n-octoxy benzophenone); methoxycinnamate; ethyl dihydroxypropyl-PABA; glyceryl PABA; homosalate (homomenthyl salicylate); meradimate (menthyl anthranilate); octocrylene (2-ethylhexyl-2-cyano-3,3-diphenylacrylate); octyl dimethyl PABA; octinoxate (octyl methoxycinnamate); octisalate (octyl salicylate); avobenzone (4-t-butyl-4'-methoxy-dibenzoylmethane); ensulizone (2-phenylbenzimidazole-5-sulphonic acid); trolamine salicylate (triethanolamine salicylate); 3-(4-methylbenzylidene)-camphor; red petrolatum; and mixtures thereof.

The cosmetic agent or mixture of cosmetic agents typically comprises about 1 wt % to about 40 wt % of the cosmetic composition, more typically about 2 wt % to about 15 wt % of the composition. The amount will depend on the particular effect or effects desired and the activity of the cosmetic agent.

When the cosmetic composition is a sunscreen composition, the amount of sunscreen agent will depend on the sunscreen agent or agents used as well as on the desired sun protection factor (SPF). SPF, which indicates the amount of protection provided by the sunscreen composition, is the ratio of the exposure time required to attain an erythema-forming threshold (barely noticeable redness) on human skin protected by the sunscreen composition to the time required to attain the erythema-forming threshold in the absence of the sunscreen composition. The higher the desired SPF, the greater the total amount of sunscreen agents required. A sunscreen composition with a SPF of 2 to under 12 provides minimal sun protection. A sunscreen composition with a SPF of 12 to under 30 provides moderate protection. A sunscreen composition with a SPF of 30 or greater provides high protection. Preferably, the sunscreen agents are included at about 4 wt % to about 35 wt % to achieve a SPF of 2 to 50. SPF may be determined as described in the *Federal Register*, Aug. 25, 1978, 43 (166), 38259-38269 ("Sunscreen Drug Products for Over-The-Counter Human Use", Food and Drug Administration). SPF values can also be approximated using in vitro models as described, for example, in *J. Soc. Cosmet. Chem.* 40:127-133 (May/June 1989) or the COPILA protocol (Test Method 94/289 Sun Protection Factor Test Method published by the Europea cosmetics, Toiletry and Perfume Association, Brussels, Belgium, October 1994.

The cosmetic composition comprises an emulsifier or mixture of emulsifiers, which can include any of a wide variety of nonionic, cationic, anionic, and zwitterionic emulsifiers or surfactants, such as ethoxylated alcohols, fatty acid amides, fatty acid esters of polyethylene glycol, fatty esters of polypropylene glycol, polyoxyethylene fatty ether phosphates, and soaps. Suitable emulsifiers include any agent useful for maintaining a stable emulsion. These include, for example, ethoxylated and propoxylated alcohols, especially $C_{10-20}$ alcohols with 2 to 100 moles of ethylene oxide and/or propylene oxide per mole of alcohol, such as steareth-10, steareth-20, laureth-5; laureth-9; laureth-10; laureth-20, ceteth-2; ceteth-4; ceteth-10; ceteth-12; ceteth-16; ceteth-20, trideceth-6 ceteareth-9, ceteareth-20, and oleth-20; polyethylene glycol 20, PPG-2; PEG-75 stearate; PEG 100 stearate; glyceryl stearate; cetyl phosphate; diethanolamine cetyl phosphate; dimethicone copolyol phosphate, hexadecyl D-glucoside; octadecyl D-glucoside; and sorbitan esters such as sorbitan oleate, sorbitan sesquioleate, sorbitan isostearate, sorbitan trioleate. Typically, the emulsifier or mixture of emulsifiers comprises about 0.2 wt % to about 10 wt %, preferably from about 3 wt % to about 7 wt % of the cosmetic composition.

The composition may also comprise one or more other ingredients that are conventional components of cosmetic compositions, such as waterproofing agents, preservatives, antioxidants, perfumes and fragrances, colorants (dyes and pigments), plant extracts, absorbents, conditioners, anti-microbial agents, insecticides, pH adjusters and buffers, and preservatives.

Cosmetic compositions, especially sunscreen compositions, that are waterproof are particularly desirable. Ingredients to enhance the water-proof nature of the composition ("waterproofing agents") may also be included such as, for example, compounds which form polymeric films such as the $C_{30}$-$C_{38}$ olefin/isopropyl maleate/MA copolymer, dimethicone copolyol phosphate, diisostearoyl trimethylolpropane siloxysilicate, chitosan, dimethicone, polyethylene, PVP, and poly(vinylpyrrolidone/vinylacetate), PVP/eicosene copolymer, adipic acid/diethylene glycol/glycerin crosspolymer, etc. When present, the composition typically comprises about 0.2 wt % to about 5 wt % of the waterproofing agent or mixture of waterproofing agents.

A preservative protects the cosmetic composition from microbial contamination and/or oxidation. Typical preservative/antioxidants are, for example, diazolidinyl urea; iodopropynl butylcarbamate; vitamin E (alpha-tocopherol) and its derivatives including vitamin E acetate (alpha-tocopherol acetate); vitamin C (ascorbic acid); butylated hydroxytoluene (BHT); butylated hydroxyanisole (BHA); esters of p-hydroxy benzoic acid such as methylparaben (p-hydroxybenzoic acid methyl ester), ethylparaben (p-hydroxybenzoic acid ethyl ester), propylparaben (p-hydroxybenzoic acid n-propyl ester), and butylparaben (p-hydroxybenzoic acid n-butyl ester); and mixtures thereof. When present, the preservative or mixture of preservatives typically comprises about 0.5 wt % to about 1.5 wt %, preferably about 0.5 wt % to about 1 wt % of the cosmetic composition. The cosmetic composition may also comprise effective amounts of one or more cosmetic adjuncts, such as colorants; perfumes and fragrances; and plant extracts such as *Aloe vera*, witch hazel, cucumber, etc.

In addition to the ingredients listed above, the balance of the cosmetic composition is water, typically deionized water. The composition typically comprises about 55 wt % to about 80 wt %, preferably about 60 wt % to about 70 wt % of water. A water content greater than about 80% may result in instability due to phase separation. A water content less than about 55% may result in instability due to phase separation and may result in an unsprayable formulation due to an increase in viscosity and a decrease in thixotropy.

If necessary, an effective amount of a pH adjuster, or buffer, may be present to adjust the pH of the cosmetic composition to the desired pH, which will vary depending on the intended use, but is typically to about 6.0 to about 7.8 for sunscreen compositions. Typical pH adjusters; are for example, sodium hydroxide, triethanolamine, citric acid and its salts, and ethylenediamine tetraacetic acid and its salts. Ethylenediamine tetraacetic acid is also a chelating agent and can chelate metal ions.

The cosmetic composition may be a self-tanning composition, that is a composition for artificially tanning the skin, such as are disclosed in Punto, U.S. Pat. No. 5,662,890, incorporated herein by reference. Self-tanning cosmetic compositions typically comprise about 2.5 wt % to about 10 wt % of a self-tanning agent, preferably dihydroxyactone, and from about 5 wt % to about 75 wt % of one or more penetration enhancers, such as dimethyl isosorbide and/or diethyl glycol monoethyl ether, as well as other optional ingredients such as perfumes, preservatives, emollients, antiseptics, pigments, dyes, sunscreen agents, and humectants, in an aqueous base, which is typically free of oil or alcohol.

A cosmetic composition may be prepared by a method that produces a homogeneous composition, typically an oil-in-water emulsion, that spreads into a film when sprayed on the skin and/or hair. These techniques, and the equipment for carrying out these techniques, are well known in the art. Preferably, for proper dispersion of the microcrystalline cellulose, it should be added and dispersed in water before the other ingredients are added.

In the preparation of a sunscreen composition, in general, a first phase containing the rheology control agent in water is prepared by dispersing the rheology control agent in the water with high speed stirring. Water-soluble emollients, such as glycerin, may also be included in this phase. Sunscreen agents can be added to either the first phase or the second phase. The first phase may be heated to about 70° C. to about 80° C. during this process.

A second phase containing all the other ingredients except the fragrance and the preservative is prepared by adding these ingredients to water with gentle stirring and heating at a temperature of from about 55° C. to about 80° C. The first phase is slowly added to the second phase while stirring at high speed and the resulting mixture gently homogenized at about 35° C. to about 70° C. to form an oil-in-water emulsion. Preservative and fragrance, if present, are added, and the emulsion is gently stirred until the temperature is below about 35° C., typically about 25° C. to about 30° C. before packaging.

The cosmetic compositions, such as sunscreen compositions, may be packaged in a suitable container, typically a non-aerosol spray device. Spray pumps such as the Eurogel Spray Pump (Seqquist Perfect, Cary Ill., USA), the P1 spray pump (Precision, Ajax, Canada), Calmar Spray Pumps, (Calmar, City of Industry, Calif., USA), and the SP20410/D/ST1 spray pump (Raepak Limited, Wymondham, Norfolk, UK) may be used. Spray pumps typically generate a shear of about $1000 \text{ s}^{-1}$ to $3000 \text{ s}^{-1}$, more typically about $1500 \text{ s}^{-1}$ to $2500 \text{ s}^{-1}$, in the nozzle region.

INDUSTRIAL APPLICABILITY

Microcrystalline cellulose has general applicability in a variety of sprayable cosmetic compositions that require uniform application of a fine mist such as sprayable creams, lotions or foams for skin, and hair applications. The spray may be left on the skin and hair (such as a pre-sun or post-sun spray treatment) or applied for a short time and then removed (such as dilipatories).

Microcrystalline cellulose is especially suited for the preparation of sprayable sunscreen compositions. Microcrystalline cellulose can be used to improve spray characteristics and prevent streaking in sprayable cosmetic compositions for artificially tanning the skin ("self-tanners"). These cosmetic compositions may be applied to the skin and/or hair in an atomized droplet form with any device having spraying means, including suitable aerosol or non-aerosol spray devices.

Microcrystalline cellulose is especially suited to the preparation of waterproof cosmetic compositions. As illustrated by the examples below, inclusion of microcrystalline cellulose allows the formulation of compositions that are stable to storage while having lower emulsifier levels than compositions stable to storage prepared without microcrystalline cellulose. Once the composition has been applied to the skin and dried, the lower emulsifier levels in compositions containing microcrystalline cellulose reduce the tendency for re-emulsification of the oil-phase when the skin is re-wetted.

The advantageous properties of this invention can be observed by reference to the following examples, which illustrate but do not limit the invention.

EXAMPLES

Materials

| INCI name | Tradename | Supplier | Function |
|---|---|---|---|
| Glycerin | Pricerine 9083 | Uniqema | Humectant |
| Propylene glycol | Propylene glycol | Merck | Moisturizer |
| Dihydroxyacetone | Dihydroxyacetone | Merck | Self-tanning agent |
| Microcrystalline cellulose and cellulose gum[a] | AVICEL ® CL 611 | FMC BioPolymer | Stabilizer and spray control agent |
| Microcrystalline cellulose and cellulose gum[a] | AVICEL ® PC 611 | FMC BioPolymer | Stabilizer and spray control agent |

-continued

Materials

| INCI name | Tradename | Supplier | Function |
|---|---|---|---|
| $C_{12}$-$_{15}$ alkyl benzoate | FINSOLV ® TN | Finetex | Emollient |
| Cylcomethicone | Fluid 245 | Dow Corning | Emollient |
| Ethylhexyl methoxycinnamate | ESCALOL ® 557 | ISP | Sunscreen agent |
| Benzophenone-3 | ESCALOL ® 567 | ISP | Sunscreen agent |
| Ethylhexyl salicylate | ESCALOL ® 587 | ISP | Sunscreen agent |
| Cetearyl alcohol | Tego Alkanal 1618 | Goldschmidt | Emulsifier |
| Ceteth 20 | BRIJ ® 58 | Uniqema | Emulsifier |
| D-Panthenal | Panthenol | BASF | Skin conditioner |
| Tocopheryl acetate | Tocopheryl acetate | Roche | Antioxidant |
| Glyceryl stearate | Kemester 5500 | Witco | Emulsifier |
| Oleth 20 | BRIJ ® 98V | Uniqema | Emulsifier |
| methylparaben | | | Preservative |
| Propylparaben | | | Preservative |
| Fragrance | Varadero DC 10007/1 | Haarmann and Reimer | Fragrance |
| Fragrance | Skin Soft | Independent Fragrance Co. | Fragrance |
| Preservative | Germaben II[b] | ISP | Preservative |
| Titanium dioxide | UV-TITAN ® | Kemira | Sunscreen agent |
| Xanthan gum | Keltrol T | CP Kelco | Thickener |
| Zinc oxide | Zinc Oxide Neutral | Haarmann and Reimer | Sunscreen agent |

[a]AVICEL ® CL 611 and AVICEL ® PC 611 are each microcrystalline cellulose and sodium carboxymethylcellulose (85/15, by weight).
[b]Mixture of propylene glycol, diazolidinyl urea, methylparaben (p-hydroxybenzoic acid methyl ester) and propylparaben (p-hydroxybenzoic acid methyl n-propyl ester).

Preparation of the Sunscreen Cosmetic Compositions

Unless otherwise indicate, the following procedures were used in the Examples.

Phase A. Water was mixed with glycerin if glycerin was present in the composition. AVICEL® CL 611 was dispersed in the water or water/glycerin by mixing with a Silverson rotor-stator mixer at high speed (8,000-10,000 rpm) for 5 minutes. If Phase A contained xanthan gum, it was dispersed into the dispersion by high shear mixing with the Silverson mixer for 5 minutes. If phase A contained an inorganic sunscreen, its was dispersed into the dispersion by mixing with the Silverson mixer at high speed for 5 minutes. The dispersion was then heated to 75° C. In all cases, the water used was deionized water.

Phase B. All ingredients in Phase B were mixed by hand stirring with a spatula. If an inorganic sunscreen was included in Phase B, it was added to Phase B as the last ingredient and mixed in using a magnetic stirrer. Phase B was then heated to 75° C. and added slowly to Phase A. The resulting mixture was then homogenized with a pre-warmed rotor-stator mixer at high speed (8,000-10,000 rpm) for 5 minutes. The mixture, containing an oil-in-water emulsion, was then cooled to 50° C. while stirring slowly with a magnetic stirrer.

Phase C was added to the emulsion and slow stirring continued until the temperature was below 35° C. The samples were packaged into 100 mL tubular plastic bottle equipped with finger-pump spray nozzles (product code SP20410/D/ST1, Raepak Limited, Wymondham, Norfolk, UK).

Evaluation Methods

Equipment A TA Carrimed $CSL^2 100$ rheometer, equipped with a 6 cm flat acrylic plate set to a gap of 500 microns, was used for all rheology testing. All samples were equilibrated on the rheometer for 20 min prior to testing to allow time for the samples to recover from shear due to handling.

Flow tests A shear rate of 1/sec was applied to the sample. The viscosity recorded after 10 sec was designated the 'Initial viscosity'. The viscosity was recorded while the shear rate was increased from 1/sec to 2000/sec over a 10 sec period. The reading at 2000/sec was recorded as the 'high shear viscosity'. Immediately thereafter, the shear rate was returned to 1/sec and the viscosity recorded at 10 sec was designated the 'recovered viscosity'.

Run-down Time A single burst of spray was delivered to a flat vertical surface (laminated wood coated with a plastic coating) placed 10 cm from the spray nozzle. The time taken for any part of the spray to travel down a distance of 4 cm was recorded. The 'run-down time' was determined as the average of three tests per sample. If the time taken was greater than 300 sec, the run-down time was recorded as '>300 sec'.

Spray Characteristic The shape and size of the spray pattern immediately after spraying was recorded as the 'spray characteristic'. The diameter of the pattern was measured as the average of three tests. Spray patterns were classified as 'even' if the spray extended evenly over a wide area. If the spray was deposited in a collection of small individual drops, the pattern was classified as uneven.

Stability Portions of each sample were stored in sealed glass containers for 21 days at 25° C. and for 7 days at 52° C. to assess stability.

SPF (sun protection factor) was determined according to the COLIPA protocol (Test method 94/289—Sun Protection Factor Test Method published by the Europea Cosmetics, Toiletry and Perfume Association, Brussels, Belgium, October 1994), but using only 5 to 6 volunteers as a screening study rather than the minimum of 10 volunteers specified by the test method.

Oscillation tests The strain was set at 1% and the frequency at 1 Hz. The 'initial storage modulus' was recorded as the G' value after 10 sec of testing on an equilibrated sample. The 'recovered storage modulus' was recorded as the G" value at 10 sec after submitting the sample to an increasing shear rate of 1/sec to 2000/sec over a 10 sec period.

Example 1

This example illustrates a sprayable sunscreen composition comprising organic sunscreen agents. The following sunscreen composition was prepared by the procedure described above.

| COMPOSITION | | |
|---|---|---|
| Ingredient | Function | wt % |
| Phase A | | |
| Water | | 63.25 |
| Glycerin | Humectant | 2.0 |
| AVICEL ® CL 611 | Rheology control agent | 1.5 |
| Phase B | | |
| $C_{12-15}$ alkyl benzoate | Emollient | 6 |
| Cylcomethicone/Dimethicone | Emollient | 2 |
| Ethylhexyl Methoxycinnamate | UV Filter | 8 |
| Benzophenone-3 | UV Filter | 4 |
| Ethylhexyl salicylate | UV Filter | 5 |
| Cetearyl alcohol | Emulsifier | 0.5 |
| Panthanol | Conditioner | 1 |
| Tocopheryl acetate | Antioxidant | 0.25 |
| Glyceryl stearate | Emulsifier | 3 |

| -continued | | |
|---|---|---|
| COMPOSITION | | |
| Ingredient | Function | wt % |
| Oleth 20 | Emulsifier | 2.5 |
| Phase C | | |
| Fragrance | | 0.04 |
| Preservative | | 1 |

| RESULTS | |
|---|---|
| Initial viscosity | 3000 Pa s |
| High shear viscosity | 40 Pa s |
| Recovered viscosity | 1500 Pa s |
| Initial G' | 28 Pa |
| Recovered G' | 23 Pa |
| Stability after 21 days at 25° C. | Acceptable |
| Stability after 7 days at 52° C. | Acceptable |
| Spray characteristic | Even, 2 cm diameter |
| Run-down time | >300 sec |
| Skin-feel | Light |

The SPF (sun protection factor), measured using six volunteers, was 17.8.

Comparative Example 1

This example shows that a similar sunscreen composition that comprises xanthan gum has a lower SPF. A sunscreen composition comprising organic sunscreen agents was prepared as in Example 1, except that the 1.5 wt % AVICEL® CL 611 microcrystalline cellulose was replaced with 0.5 wt % xanthan gum and 1.0 wt % water. The resulting sunscreen composition had a heavy skin-feel. The SPF, using six volunteers, was 13.3.

Example 2

This example illustrates a sprayable sunscreen comprising a mixture of an inorganic sunscreen agent and organic sunscreen agents.

| COMPOSITION | |
|---|---|
| Ingredient | wt % |
| Phase A | |
| Deionized water | 66.5 |
| AVICEL ® CL 611 | 1.5 |
| Phase B | |
| $TiO_2$ | 5 |
| $C_{12-15}$ alkyl benzoate | 10 |
| Octyl Methoxycinnamate | 8 |
| Benzophenone-3 | 3 |
| Glyceryl stearate | 2.5 |
| Oleth 20 | 2.5 |
| Phase C | |
| Fragrance | 0.04 |
| Preservative | 1 |

| RESULTS | |
|---|---|
| Spray characteristic | Even, 2.5 cm diameter |
| Run-down time | 230 sec |
| Skin-feel | Light |

The SPF, using five volunteers, was 25.

Comparative Example 2

A sunscreen composition comprising organic sunscreen agents was prepared by as in Example 2, except that the 1.5 wt % AVICEL® CL 611 microcrystalline cellulose was replaced with 0.5 wt % xanthan gum and 1.0 wt % water. The resulting sunscreen composition had a heavy skin-feel. The SPF, using five volunteers, was 25.

Examples 3-5

These examples illustrate sprayable sunscreen compositions comprising an inorganic sunscreen agent.

| COMPOSITION | | | |
|---|---|---|---|
| Ingredient | Example 3 wt % | Example 4 wt % | Example 5 wt % |
| Phase A | | | |
| Deionized water | 79.98 | 76.98 | 71.98 |
| AVICEL ® CL 611 | 2 | 2 | 2 |
| Phase B | | | |
| Titanium dioxide | 2 | 5 | 10 |
| C12-15 alkyl benzoate | 10 | 10 | 10 |
| Glyceryl stearate | 2.5 | 2.5 | 2.5 |
| Oleth 20 | 2.5 | 2.5 | 2.5 |
| Phase C | | | |
| Fragrance | 0.02 | 0.02 | 0.02 |
| Preservative | 1 | 1 | 1 |

| RESULTS | | | |
|---|---|---|---|
| | Example 3 | Example 4 | Example 5 |
| Initial viscosity | 3400 Pa-s | 4000 Pa-s | 15000 Pa-s |
| High shear viscosity | 45 Pa-s | 41 Pa-s | 60 Pa-s |
| Recovered viscosity | 1200 Pa-s | 1100 Pa-s | 3300 Pa s |
| Stability after 21 days at 25° C. | Acceptable | Acceptable | Acceptable |
| Stability after 7 days at 52° C. | Acceptable | Acceptable | Acceptable |
| Spray characteristic | Uneven 4.5 cm dia. | Uneven 5 cm dia. | Uneven 4 cm dia. |
| Run-down time | >300 sec | >300 sec | >300 sec |

Example 6

This example illustrates a sprayable sunscreen composition comprising an inorganic sunscreen agent.

| COMPOSITION | |
|---|---|
| Ingredient | wt % |
| Phase A | |
| Deionized water | 66.5 |
| AVICEL ® CL 611 | 1.5 |
| Zinc oxide | 5 |
| Phase B | |
| $C_{12-15}$ alkyl benzoate | 10 |
| Octyl Methoxycinnamate | 8 |
| Benzophenone-3 | 3 |
| Glyceryl stearate | 2.5 |
| Oleth 20 | 2.5 |
| Phase C | |
| Preservative | 1 |

| RESULTS | |
|---|---|
| Stability after 21 days at 25° C. | Acceptable |
| Stability after 7 days at 52° C. | Acceptable |
| Spray characteristic | Even, 3 cm diameter |
| Run-down time | 180 sec |

Comparative Example 3

This example shows the characteristics of various commercially available sprayable sunscreen compositions. The properties of five different commercially available sprayable sunscreen compositions (Products 1-5) are reported in the table below.

| RESULTS | | | |
|---|---|---|---|
| | Product 1 | Product 2 | Product 3 |
| SPF | 30 | 30 | 12 |
| Initial viscosity | 12,500 Pa s | 500,000 Pa s | 400 Pa s |
| High shear viscosity | 80 Pa s | 150 Pa s | 40 Pa s |
| Recovered viscosity | 6,000 Pa s | 15,000 Pa s | 400 Pa s |
| Initial G' | 27 Pa | 150 Pa | 4 Pa |
| Recovered G' | 18 Pa | 100 Pa | 3 Pa |
| Spray characteristic | Even, 2.5 cm dia | Uneven, 5 cm dia | Even, 4 cm dia |
| Run-down time | 25 sec | >300 sec | 10 sec |
| Skin-feel | Heavy, sticky | Heavy | Light |
| | Product 4 | Product 5 | |
| SPF | 30 | 48 | |
| Spray characteristic | Uneven, 5 cm dia | Uneven, 9 cm dia | |
| Run-down time | >300 sec | >300 sec | |
| Skin-feel | Heavy, sticky | Heavy | |

Example 7

This example illustrates a sprayable sunscreen composition comprising organic sunscreen agents. The composition was identical to Example 1, but the procedure used differed from that of Example 1 in the following ways. Panthanol was added as the last ingredient to Phase A instead of adding it to Phase B. Phase A was heated to 85° C. Phase B was heated to 85° C.

| RESULTS | |
|---|---|
| Stability after 21 days at 25° C. | Acceptable |
| Stability after 7 days at 52° C. | Acceptable |
| Spray characteristic | Even, 3 cm diameter |
| Run-down time | >300 sec |

Comparative Examples 4 and 5

Comparative Example 4 illustrates that it is more difficult to disperse inorganic sunscreens in the aqueous phase if microcrystalline cellulose is omitted. Comparative Examples 4 and 5 illustrate that compositions that do not contain microcrystalline cellulose are less stable than formulations containing microcrystalline cellulose.

In Comparative Example 4, the procedure of Example 6 was repeated, except that microcrystalline cellulose was omitted from the composition, glyceryl stearate was 4 wt % of the composition, oleth 20 was 4 wt % of the composition, and water was 65 wt % of the composition. During preparation, it observed that was that the zinc oxide was not properly dispersed in the water phase. Although the method of preparation was identical and the composition was similar to that of Example 6, the composition was not stable to storage at 52° C. for 7 days.

In Comparative Example 5, the procedure of Comparative Example 4 was repeated except that the zinc oxide was added to the oil phase instead of the water phase. This composition was not stable to storage at 52° C. for 7 days.

Examples 8-9

This example illustrates the use of microcrystalline cellulose in sprayable moisturizing lotions. The procedure was similar to that of Example 1 except the composition given in the following table was used. The results of the evaluation are shown below.

| COMPOSITION | | |
|---|---|---|
| Ingredient | Example 8 wt % | Example 9 wt % |
| Phase A | | |
| Water | 79.4 | 79.4 |
| Propylene glycol | 5.0 | 5.0 |
| AVICEL ® CL 611 | 1.0 | 1.5 |
| Panthenol | 0.5 | 0.5 |
| Phase B | | |
| $C_{12-15}$ alkyl benzoate | 5.0 | 5.0 |
| Cylcomethicone | 2.0 | 2.0 |
| Cetearyl alcohol | 0.5 | 0.5 |
| Glyceryl stearate | 3.0 | 2.5 |
| Oleth 20 | 2.5 | 2.0 |
| Phase C | | |
| Fragrance | 0.1 | 0.05 |
| Preservative | 1.0 | 1.0 |

| RESULTS | | |
|---|---|---|
| | Example 8 | Example 9 |
| Stability at 25° C., 7 days | Acceptable | Acceptable |
| Stability at 52° C., 7 days | Acceptable | Acceptable |
| Spray characteristic | Even | Even |
| Run-down time | 180 sec | 95 sec |
| Skin-feel | Creamy, good | Creamy, good |

Comparative Example 6

This example illustrates a formulation similar to Example 8 except that no AVICEL® CL 611 was used. The resulting formulation has a much less pleasant skin-feel. In addition, the rundown time is much shorter.

| COMPOSITION | |
|---|---|
| Ingredient | wt % |
| Phase A | |
| Water | 80.4 |
| Propylene glycol | 5.0 |
| Panthenol | 0.5 |
| Phase B | |
| $C_{12-15}$ alkyl benzoate | 5.0 |
| Cylcomethicone/Dimethicone | 2.0 |
| Cetearyl alcohol | 0.5 |
| Glyceryl stearate | 3.0 |
| Oleth 20 | 2.5 |
| Phase C | |
| Fragrance | 0.1 |
| Preservative | 1.0 |

| RESULTS | |
|---|---|
| Stability at 25° C., 7 days | Acceptable |
| Stability at 52° C., 7 days | Acceptable |
| Spray characteristic | Even |
| Run-down time | 18 sec |
| Skin-feel | Light, water-like |

Examples 10-11

These examples illustrate the use of microcrystalline cellulose in sprayable self-tanning lotions. Spray application of self-tanning products is desirable because there is less contact between the hands and the lotion compared to application of lotions by massaging. Application by massaging produces staining of the hands. Sprayable products that deliver a fine mist of lotion directly to the skin, and do not run after application, are particularly desirable as they further reduce the tendency for staining of hands and clothing. In addition, these sprayable products will result in improved tanning consistency. This example also illustrates that microcrystalline cellulose is effective at stabilizing products containing dihydroxyacetone.

| COMPOSITION | | |
|---|---|---|
| Ingredient | Example 10 wt % | Example 11 wt % |
| Phase A | | |
| Water | 61.1 | 60.45 |
| AVICEL ® CL 611 | 1.0 | 1.5 |
| Phase B | | |
| C$_{12-15}$ alkyl benzoate | 5.0 | 5.0 |
| Glyceryl stearate | 2.0 | 2.0 |
| Oleth 20 | 1.5 | 1.5 |
| Cetearyl alcohol | 0.4 | 0.5 |
| Phase C | | |
| Water | 20.0 | 20.0 |
| Propylene glycol | 3.0 | 3.0 |
| Dihydroxyacetone | 5.0 | 5.0 |
| Germaben II | 1.0 | 1.0 |
| Fragrance | | 0.05 |

The self-tanning products were prepared by the following procedure.

Phase A. AVICEL® CL 611 was dispersed in water by mixing with a Silverson rotor-stator mixer at high speed (8,000-10,000 rpm) for 5 minutes. The dispersion was then heated to 75° C.

Phase B. All ingredients in Phase B were mixed by hand stirring with a spatula and then heated to 75° C. Phase A was mixed with Phase B and then homogenized with a pre-warmed rotor-stator mixer at high speed (8,000-10,000 rpm) for 5 minutes. The mix, containing an oil-in-water emulsion, was then cooled to 40° C. while stirring slowly with a propeller mixer.

Phase C. Phase C was prepared separately by dispersing dihydroxyacetone in water using a propeller mixer for 30 minutes. Propylene glycol and Germaben II were added and the mixture was heated to 40° C. Phase C was then added to the emulsion prepared form Phases A and B. The combined mixture was adjusted to the pH range of 3 to 4 using a solution of 5% citric acid, mixed with a propeller mixer for 10 minutes then cooled to room temperature.

| RESULTS | | |
|---|---|---|
| | Example 10 | Example 11 |
| Stability at 25 C., 7 days | Acceptable | Acceptable |
| Stability at 52 C., 7 days | Acceptable | Acceptable |
| Spray characteristic | Even | Even |
| Run-down time | 60 sec | 95 sec |
| Skin-feel | good | good |
| Tanning | Even | Even |
| pH after 1 h | 3.90 | 3.94 |
| pH after 4 days | 3.88 | 3.91 |

Comparative Example 7

This example illustrates that a formulation similar to Example 10, except that the AVICEL® CL 611 was omitted, has lower stability and a lower rundown time.

| COMPOSITION | |
|---|---|
| Ingredient | wt % |
| Phase A | |
| Water | 62.1 |
| Phase B | |
| C$_{12-15}$ alkyl benzoate | 5.0 |
| Glyceryl stearate | 2.0 |
| Oleth 20 | 1.5 |
| Cetearyl alcohol | 0.4 |
| Phase C | |
| Water | 20.0 |
| Propylene glycol | 3.0 |
| Dihydroxyacetone | 5.0 |
| Germaben II | 1.0 |

| RESULTS | |
|---|---|
| Stability at 25° C., 7 days | Unstable, sedimentation of white particles |
| Stability at 52° C., 7 days | Unstable, sedimentation of white particles |
| Spray characteristic | Even |
| Run-down time | 22 sec |
| Skin-feel | good |
| pH after 1 h | 3.91 |
| pH after 4 days | 4.02 |

Example 12

This example illustrates the use of microcrystalline cellulose in a self-tanning spray. The following ingredients were used.

| COMPOSITION | |
|---|---|
| Ingredient | wt % |
| Phase A | |
| Water | 20.0 |
| Dihydroxyacetone | 5.0 |
| Propylene glycol | 3.0 |
| Skin Soft (fragrance)I | 1.0 |
| Phase B | |
| C$_{12-15}$ alkyl benzoate | 5.0 |
| Glyceryl stearate | 2.0 |
| Oleth 20 | 1.5 |
| Cetearyl alcohol | 0.5 |
| Phase C | |
| Water | 61.15 |
| AVICEL ® PC 611 | 1.50 |
| Methylparaben | 0.20 |
| Propylparaben | 0.10 |

The product was prepared by the following procedure.

Phase A. Dihydroxyacetone is dispersed in water to form a homogeneous solution. The remaining ingredients are added, and the mixture heated to 40° C.

Phase B. The ingredients are combined, and the resulting mixture heated to 75° C.

Phase C. The microcrystalline cellulose is dispersed in the water using high shear (for example, rotor-stator mixer for 5 minutes). The remaining ingredients are added, and the resulting mixture heated to 75° C.

Phase B is slowly added to Phase C. The resulting mixture is homogenized and then cooled to 40° C. with constant slow mixing. If necessary, the pH is adjusted to 3.0 to 4.0 with a 20% aqueous solution of citric acid. An opaque, low viscosity lotion with a light feel and excellent color development is obtained. pH is about 3.8.

Example 13

This example illustrates the use of microcrystalline cellulose in an after-sun moisturizing spray.

| COMPOSITION | |
|---|---|
| Ingredient | wt % |
| Phase A | |
| Water | 79.95 |
| AVICEL ® PC 611 | 1.50 |
| Propylene glycol | 5.00 |
| Panthenol | 0.50 |
| Phase B | |
| $C_{12-15}$ alkyl benzoate | 5.00 |
| Glyceryl stearate | 2.50 |
| Oleth 20 | 2.00 |
| Cyclomethicone | 2.00 |
| Cetearyl alcohol | 0.50 |
| Phase C | |
| Preservative[a] | 1.00 |
| Varadero DC 10007/1 Fragrance | 0.05 |

[a]Mixture of propylene glycol, diazolidinyl urea, methylparaben, and propylparaben.

The product is prepared by the following procedure.

Phase A. The microcrystalline cellulose is dispersed in the water using high shear (for example, rotor-stator mixer for 5 minutes). The remaining ingredients are added, and the resulting mixture heated to 75° C.

Phase B. The ingredients are combined, and the resulting mixture heated to 75° C.

Phase B is slowly added to Phase A. The resulting mixture is homogenized and then cooled to 50° C. with constant slow mixing. Phase C is added at 50° C. and the resulting mixture cooled to below 30° C. with continuous slow mixing before packaging.

Example 14

This example illustrates the viscosity under different conditions of a sprayable sunscreen composition comprising organic sunscreen agents. The following sunscreen composition was prepared by the procedure described in Example 1.

| COMPOSITION | | |
|---|---|---|
| Ingredient | Function | wt % |
| Phase A | | |
| Water | | 63.20 |
| Glycerin | Humectant | 2.00 |
| AVICEL ® CL 611 | Rheology control agent | 1.50 |
| Phase B | | |
| Ethylhexyl Methoxycinnamate | UV Filter | 8.00 |

| COMPOSITION -continued | | |
|---|---|---|
| Ingredient | Function | wt % |
| $C_{12-15}$ alkyl benzoate | Emollient | 6.00 |
| Ethylhexyl salicylate | UV Filter | 5.00 |
| Benzophenone-3 | UV Filter | 4.00 |
| Glyceryl stearate | Emulsifier | 3.00 |
| Oleth 20 | Emulsifier | 2.50 |
| Cylcomethicone | Emollient | 2.00 |
| D-Panthanol | Conditioner | 1.00 |
| Cetearyl alcohol | Emulsifier | 0.50 |
| Tocopheryl acetate | Antioxidant | 0.25 |
| Phase C | | |
| Varadero DC 20007/1 | Fragrance | 0.05 |
| Germaben II | Preservative | 1.00 |

Viscosity was measured as described in the evaluation methods above. The viscosity as a function of shear rate is shown in FIG. 1. At high shear the viscosity decreases. The recovered viscosity, after the viscosity has been reduced by high shear and the high shear removed, increases as a function of time, is shown in FIG. 2. The viscosity as a function of temperature for the composition under shears of $1\ s^{-1}$, $10\ s^{-1}$, and $2000\ s^{-1}$ is shown in FIG. 3. A shear rate of $1\ s^{-1}$ simulates the composition in a container. A shear rate of $10\ s^{-1}$ simulates the composition during spreading on the skin. A shear rate of $2000\ s^{-1}$ simulates the composition passing through the nozzle of a sprayer.

Having described the invention, we now claim the following and their equivalents.

What is claimed is:

1. A sprayable composition, the sprayable composition comprising:
    a cosmetic agent or mixture of cosmetic agents selected from the group consisting of sunscreen agents, self-tanning agents, depilatories, exfoliating agents, and mixtures thereof;
    an emulsifier or mixture of emulsifiers;
    a rheology control agent; and
    55-80 wt % water based on the total weight of the sprayable composition;
    in which:
    the cosmetic agent or mixture of cosmetic agents comprises about 0.1 wt % to 40 wt % of the composition;
    the emulsifier or mixture of emulsifiers comprises about 0.2 wt % to about 20 wt % of the composition;
    the rheology control agent comprises about 0.2 wt % to about 3 wt % of the composition;
    the rheology control agent comprises coprocessed microcrystalline cellulose and carboxymethylcellulose, wherein said coprocessed microcrystalline cellulose has an average particle size of 50 microns or less;
    the composition has a viscosity at high shear of 120 Pa·s or less; and
    wherein said composition is sprayable in a non-aerosol spray device.

2. The composition of claim 1 in which the composition has a viscosity at high shear of 100 Pa·s or less.

3. The composition of claim 1 or claim 2 in which the cosmetic agent or mixture of cosmetic agents comprises about 2 wt % to about 20 wt % of cosmetic agents selected from the group consisting of emollients, occlusive agents, moisturizers, and humectants.

4. The composition as in any one of claims 1-2 in which the coprocessed microcrystalline cellulose has an average particle size of below 10 microns.

5. The composition as in any one of claims 1-2 in which the microcrystalline cellulose is a water-dispersible microcrystalline cellulose.

6. The composition of claim 1 in which the coprocessed microcrystalline cellulose comprises the microcrystalline cellulose and sodium salt of carboxymethylcellulose in a ratio of about 85/15, by weight.

7. The composition as in any one of claim 1-2 or 6 in which the coprocessed microcrystalline cellulose has an average particle size of below 1 micron.

8. The composition as in any one of claim 1-2 or 6 in which the cosmetic agent comprises a sunscreen agent or a mixture of sunscreen agents.

9. The composition of claim 8 in which the sunscreen agent or mixture of sunscreen agents comprises an inorganic sunscreen agent or a mixture of inorganic sunscreen agents.

10. The composition as in any one of claim 1-2 or 6 in which the sunscreen agent or mixture of sunscreen agents comprises an organic sunscreen agent or a mixture of organic sunscreen agents.

11. The composition of claim 8 in which the composition has a sun protection factor of at least 12.

12. The composition of any one of claim 1 to 2 or 6 in which the composition comprises a self-tanning agent.

13. The composition as in any one of claim 1-2 or 6 in which the composition has a viscosity at a high shear of 80 Pa-s or less.

14. The composition as in any one of claim 1-2 or 6 in which the composition has a rundown time of 100 seconds or greater.

15. A method for applying a cosmetic composition, the method comprising the step of spraying the cosmetic composition in any one of claim 1-2 or 6 onto the skin, onto the hair, or onto the skin and the hair.

* * * * *